United States Patent [19]

Colborn

[11] Patent Number: 4,855,467

[45] Date of Patent: Aug. 8, 1989

[54] HEAT CURABLE EPOXY COMPOSITIONS, AND AMINE ADDUCTS OF COBALT(II) COMPLEXES

[75] Inventor: Robert E. Colborn, Schenectady, N.Y.

[73] Assignee: General Electric Company, Schenectady, N.Y.

[21] Appl. No.: 284,020

[22] Filed: Dec. 14, 1988

Related U.S. Application Data

[62] Division of Ser. No. 191,639, May 9, 1989, Pat. No. 4,814,391.

[51] Int. Cl.$^4$ .............................................. C07F 15/06
[52] U.S. Cl. ....................................................... 556/40
[58] Field of Search .......................................... 556/40

[56] References Cited

U.S. PATENT DOCUMENTS

| | | | |
|---|---|---|---|
| 3,812,214 | 5/1974 | Markovitz | 528/92 |
| 3,888,895 | 6/1975 | Manning et al. | 556/40 |
| 4,086,091 | 4/1978 | Cella | 528/92 X |
| 4,113,791 | 9/1978 | Smith | 528/92 X |
| 4,137,275 | 1/1979 | Smith et al. | 528/92 |
| 4,337,210 | 6/1982 | Van der Maas | 556/40 |
| 4,400,676 | 8/1983 | Mitsui | 528/92 X |

*Primary Examiner*—Earl Nielsen
*Attorney, Agent, or Firm*—William A. Teoli; James C. Davis, Jr.; William H. Pittman

[57] ABSTRACT

Certain cobalt(II) complexes such as secondary amine adducts of cobalt(II) acetylacetonate have been found useful as latent catalysts for anhydride-epoxy blends.

6 Claims, No Drawings

HEAT CURABLE EPOXY COMPOSITIONS, AND AMINE ADDUCTS OF COBALT(II) COMPLEXES

This application is a divison of U.S. patent application Ser. No. 191,639, filed May 9,1988, U.S. Pat. No. 4,814,391.

BACKGROUND OF THE INVENTION

Prior to the present invention, various procedures were used to cure epoxy resins. For example, Crivello, U.S. Pat. No. 4,058,401, shows that epoxy resins can be cured by use of a photoinitiator, such as a triarylsulfonium salt, in combination with actinic radiation such as ultraviolet light. Heat curable epoxy resins are often preferred in particular applications, particularly where exposure to radiation to activate a photoinitiator is not feasible. The use of anhydride cured epoxy resins in the electrical industry is widespread for insulating electrical parts due to the excellent mechanical and electrical properties of the cured resin. In U.S. Pat. No. 4,511,701 (Ryang), there is shown the use of a silyl norbornane functional anhydride which has been found to provide excellent physical properties when used in combination with a small amount of organic amine such as benzylethylamine. However, a mixture of the epoxy resin, anhydride, and amine accelerator cures rapidly on mixing. In the absence of an amine accelerator, a mixture of the silyl norbornane anhydride and the epoxide resin has been found to be stable for a year under ambient conditions.

Latent cures of epoxy resins also have been used to some degree. For example, boron trifluoride-monoethylamine complex has been used as well as various metal salts and a variety of phosphonium and ammonium salts as shown by U.S. Pat. Nos. 3,784,583 and 3,978,026. A further strategy to use a latent amine is the employment of urethanes as shown by U.S. Pat. No. 4,111,917 but the expulsion of $CO_2$ makes this system impractical for many applications. The use of metal acetylacetonates is shown by U.S. Pat. No. 4,254,351.

It would be desirable, therefore, to provide a heat curable mixture of epoxy resin and anhydride which would be stable under ambient conditions for an indefinite period of time, such as 6 months or more, and which would cure within 30 minutes at a temperature in the range of from 150° C. to 200° C.

The present invention is based on the discovery that certain amine adducts of cobalt (II) acetylacetonate and, preferably, secondary diamine adducts, for example, the adduct with di-N-butyl ethylenediamine has been found to provide shelf stabilities in excess of 6 months under ambient conditions and can be converted to a thermoset within 3 minutes at 190° C.

STATEMENT OF THE INVENTION

There is provided by the present invention, heat curable epoxy compositions comprising, by weight,
(A) 100 parts of epoxy resin,
(B) up to 200 parts of organic anhydride, and
(C) 0.01 to 20 parts of an amine adduct of cobalt(II) acetylacetonate.

The term "epoxy resin" as utilized in the description of the curable compositions of the present invention, includes any monomeric, dimeric or oligomeric or polymeric epoxy material containing one or a plurality of epoxy functional groups. For example, those resins which result from the reaction of bisphenol-A (4,4'-isopropylidenedephenol) and epichlorohydrin, or by the reaction of low molecular weight phenol-formaldehyde resins (Novolak resins) with epichlorohydrin, or by the reaction of low molecular weight phenol-formaldehyde resins (Novolak resins) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy-siloxane resins, epoxy-polyurethanes and epoxy-polyesters. Such polymers usually have epoxy functional groups at the ends of their chains. Epoxy-siloxane resins and methods for making are more particularly shown by E. P. Pluedemann and G. Fanger, J. Am. Chem. Soc. 81 632–5 (1959). As described in the literature, epoxy resins can also be modified in a number of standard ways such as reactions with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,850; 3,567,797; 3,677,995; etc. Further examples of epoxy resins which can be used are shown in the Encyclopedia of Polymer Science and Technology, 6 (1967), Interscience Publishers, New York, pp. 209–271.

Organic anhydrides which can be used in the practice of the present invention, is preferably 5,5'-(1,1,3,3-tetramethyl-1,3-disiloxanedilyl)-bis-norbornane-2,3-dicarboxylicanhydride. However, other anhydrides can be employed such as benzophenone dianhydride, bisphenol-A dianhydride, pyromellitic dianhydride, and monoanhydrides such as hexahydrophthylic anhydride, phthalic anhydride, and maleic anhydride. Mixtures of the aforementioned anhydrides and the aforementioned bisnorbornane disiloxane dianhydride also have been found effective.

Although products of cobalt(II) acetylacetonates and bases have been known prior to the present invention, as shown by W. Biltz, J. A. Clinch, Z. Anorg. Alg. Chem. 40, (1904) 221, it has been found that many of such cobalt(II) base adducts did not provide either the solubility or the shelf life required. It has been found, however, that tertiary diamine adducts of $\beta$-diketonates of cobalt(II) provide effective results. Some of the tertiary diamines, for example, are tetramethylethylenediamine(TMEDA) and tetraethylethylenediamine(TEEDA). However, it has been found that adducts of secondary diamines, such as N,N'-di-t-butylethylenediamine(DTBDA), provide significantly longer shelf lives for curable compositions utilized in accordance with the practice of the present invention.

Among the amines which can be used to make adducts of cobalt(II) acetylacetonates within the practice of the invention there are included monoamines such as,
pyridine and imidazole,
primary monoamines such as methylamine, ethylamine, benzylamine, aniline, picoline;
secondary monoamines, such as dimethylamine, diethylamine, methylbenzylamine, N-methylaniline, dipentylamine, piperidine;

tertiary monoamines, such as trimethylamine, quinuclidine, N,N-dimethylbenzylamine;

diamines, which include mixed systems such as aminopyridines, dipyridines, N,N-dimethylethylenediamine, N-methylethylenediamine;

primary diamines such as ethylenediamine (1,2-diaminoethane), propylenediamines (1,2-diaminopropane, 1,3-diaminopropane);

secondary diamines such as N,N'-dimethylethylenediamine N,N'-di-n-butylethylenediamine, N,N'-di-t-butylethylenediamine;

tertiary diamines such as N,N,N',N'-tetramethylethylenediamine (TMEDA), N,N,N',N'-tetraethylethylenediamine (TEEDA);

and nitrogen-based heterocycles such as triazines, triazoles, etc.

Preferably, the cobalt(II) acetylacetonate adducts of the present invention are the adducts of chelating secondary diamines. These have the long shelf stability required for many applications. However, the tertiary amines do provide latency if a faster reaction is needed.

The preparation of the cobalt(II) acetylacetonate adducts is generally effected by initially dissolving the cobalt acetylacetonate in freshly distilled toluene and heating it to a temperature of about 110° C. to effect the removal of any residual bound water. Amine is then added when refluxing has subsided. The amine is usually added in 10% excess. If the ligand is a solid, it can be added in a portion of toluene. The product can be immediately filtered from the reaction mixture upon cooling and crystallized from the solution after removal of some of the solvent. Recrystallization may be effected from a hexene/toluene mixture at −20° C.

The heat curable compositions of the present invention can be made by initially combining the epoxy resin and the anhydride to form a substantially uniform mixture. In instances where the anhydride is a bisnorbornanedisiloxane, heating to a temperature of 120°–150° C. can facilitate the dissolution of the anhydride into the epoxy resin. Incorporation of the amine adduct into the resulting epoxy resin mixture can be achieved by adding the catalyst at room temperature with stirring in a conventional manner.

Depending upon the nature of the anhydride, that is whether it is a norbornane anhydride or dianhydride functional siloxane, or whether the value of n in the organosiloxane block has a value of from 1 to 50, or 1000 or higher, the amount and the manner by which cure of the resulting epoxy resin composition is achieved can vary widely. It has been found, for example, that effective results can be achieved if sufficient anhydride is employed to provide at least from 0.01 to 10 moles of anhydride, per mole of oxirane oxygen of the epoxy resin.

The heat curable epoxy resin compositions of the present invention can be applied onto to various substrates such as glass, steel, aluminum, and wood, and are useful as molding and potting compounds, adhesives, coatings, and sealants.

In order that those skilled in the art will be better able to practice the invention, the following examples are given by way of illustration and not by way of limitation. All parts are by weight.

EXAMPLE I

A mixture of 23 parts of 5,5'-(1,1,3,3-tetramethyl-1,3-disiloxanediyl)-bisnorbornane-2,3-dicarboxylic anhydride and 17 grams of Epon 825 was heated and stirred to form a homogeneous solution. After the solution had cooled to a viscous fluid, 0.8 gram of cobalt-(acetylacetonate)$_2$ tetraethylethylenediamine (TEEDA) was incorporated at 2% by weight. The resulting homogeneous liquid was then poured into a preheated mold and placed in an oven at 180° C. The samples were usually removed after 30 minutes and postbaked for 16 hours. It was independently determined that full cure was reached after 2 hours. The resulting cured product had a heat distortion temperature of 295° C.

The same procedure was repeated except that in place of a cobalt acetylacetonate(TEEDA) there was used several additional amine adducts of cobalt(II) acetylacetonate. The following results were obtained, where MePY is 2-amino-6-methylpyridine, DIPY is 2,2'-dipyridine, Aminopy is 2-aminopyridine, and TMEDA is 1,3-tetramethylethylenediamine:

| | Cobalt (II) Catalysts | | |
|---|---|---|---|
| | Time to Gelation (minutes) | | |
| Compound | 90° | 150° | Solubility |
| Blank | >3000 | 320 | Good |
| 1 Co(acac)$_2$(diisobutylamine)$_2$ | 2351 | 28 | Good |
| 2 Co(acac)$_2$ | 2306 | 25 | Good |
| 3 Co(acac)$_2$(N,N'—di-t-butylethylenediamine) | 1703 | 42 | Good |
| 4 Co(acac)$_2$(1,2-Diaminopropane) | 1172 | 35 | Poor |
| 5 Co(acac)$_2$(1,2-Diaminobenzene) | 626 | 21 | Slight |
| 6 Co(acac)$_2$(2-Amino-6-MePY) | 494 | 24 | Good |
| 7 Co(acac)$_2$(N,N'—di-n-butylethylenediamine) | 449 | 23 | Good |
| 8 Co(acac)$_2$(DIPY) | 242 | 25 | Good |
| 9 Co(acac)$_2$(N,N—Dimethylethylenediamine) | 223 | 8 | Good |
| 10 Co(acac)$_2$(1,3-Tetramethylpropanediamine) | 219 | 12 | Slight |
| 11 Co(acac)$_2$(2-Aminopy) | 179 | 50 | Good |
| 12 Co(acac)$_2$(TMEDA) | 157 | 7 | Good |
| 13 Co(acac)$_2$(TEEDA) | 111 | 9 | Good |
| 14 PPh$_3$ | 39 | 4 | Good |
| 15 TMEDA | 28 | 3 | Good |

The above results show that the secondary amine adducts (1,3,7) have the best balance between shelf stability, solubility, and rapid cure at elevated temperatures. While the Co(acac)$_2$(2) shows substantial latency, the cured material does not show equivalent properties to those based on the amines (vide infra). It can also be deduced that those complexes with tertiary amines (9, 10, 12, 13) show considerable latency with respect to conventional catalysts (14, 15) but not to the extent of the secondary amines. The primary amines bind tightly to the metal center (4, 5) but suffer from poor solubility in the resin.

EXAMPLE II

Several secondary diamine adducts of cobalt(II) acetylacetonate were prepared by adding 1.04 grams (4 millimoles) of cobalt acetylacetonate into a 50 ml two-necked flask. There was then added 30 ml of freshly distilled toluene along with a stir bar. The mixture was heated and residual water bound to the cobalt acetylacetonate was azotropically removed. When the distillation temperature reached 110° C., heating of the mixture was discontinued. There was then added 0.76 grams (4.4 millimoles) of N,N'-dibutylethylenediamine when the refluxing had subsided. The solution was stirred for one hour and allowed to cool. The product was crystallized from the solution after removal of some of the solvent by rotoevaporation. Recrystallization was effected from a hexane/methylenechloride mixture at −20° C. The same procedure was repeated except that in place of N,N'-di-t-butylethylenediamine there was added N,N'-t-N-butylethylenediamine. The following results were obtained:

$Co(acac)_2$(N,N'-di-t-butylethylenediamine) red-purple solid; n.p. 92° C.; field desorption mass spectrometry indicated a parent molecular ion at 429; IR ($cm^{-1}$) 3245, 1590, 1508, 404. Analysis calculated: C, 55.93; H, 8.91; N, 6.52, Found. C, 55.90; H, 8.35; N, 6.10.

$Co(acac)_2$(N,N'-d-n-butylethylenediamine) purple oil; field desorption mass spectrometry indicated a parent molecule ran at 429. IR ($cm^{-1}$) 1597, 1518, 419. Analysis calculated: C, 55.93; H, 8.91; N, 6.52. Found. C, 55.47; H, 8.76; N, 6.05.

The above adducts were found to be useful as latent curing catalysts for epoxy anhydride blends as shown in Example 1.

EXAMPLE III

Following the procedure of Example II, several tertiary diamine adducts of cobalt(II) acetylacetonate were prepared. There was obtained $Co(acac)_2$(TMEDA) which is the cobalt(II) adduct of tetramethylethylenediamine having a pink-red color, M.P. 88° C., % C51.95(51.47) % H 7.88 (8.10) % N 7.01 (7.50).

$Co(acac)_2$(TEEDA) which is the cobalt(II) adduct of tetraethylethylenediamine having a red color, M.P. 66° C., A.C. 56.03 (55.93) % H 8.78 (8.91) % N 6.27 (6.52). Both adducts were found to be valuable latent curing catalysts.

Although the above examples are directed to only a few of the very many variables which can be used in the practice of the present invention, it should be understood that the present invention is directed to a much broader variety of curable compositions and Lewis base adducts of cobalt(II) acetylacetonate as shown in the description preceding these examples.

What is claimed and sought to be protected by Letters Patent of the United States is as follows:

1. An adduct of cobalt(II) acetylacetonate and a tertiary organic diamine.
2. An adduct of cobalt(II) acetylacetonate and a tertiary organic monoamine.
3. $Co(acac)_2$(N,N'-di-t-butylethylenediamine).
4. $Co(acac)_2$(N,N'-di-n-butylethylenediamine).
5. $Co(acac)_2$(tetramethylethylenediamine).
6. $Co(acac)_2$(tetraethylethylenediamine).

* * * * *